(12) United States Patent
Pujado

(10) Patent No.: US 7,998,893 B2
(45) Date of Patent: Aug. 16, 2011

(54) TREATMENT OF AIR TO A CATALYST REGENERATOR TO MAINTAIN CATALYST ACTIVITY

(75) Inventor: Peter R. Pujado, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 1069 days.

(21) Appl. No.: 11/681,456

(22) Filed: Mar. 2, 2007

(65) Prior Publication Data

US 2007/0207915 A1    Sep. 6, 2007

Related U.S. Application Data

(63) Continuation-in-part of application No. 11/287,032, filed on Nov. 22, 2005, now abandoned.

(51) Int. Cl.
*B01J 38/04* (2006.01)
(52) U.S. Cl. .............................. 502/34; 502/38; 502/516
(58) Field of Classification Search .................... 502/34, 502/38, 49, 50, 51, 52, 53, 55, 56, 514, 516
See application file for complete search history.

(56) References Cited

U.S. PATENT DOCUMENTS

| | | | |
|---|---|---|---|
| 2,882,243 A | 4/1959 | Milton | 252/455 |
| 2,882,244 A | 4/1959 | Milton | 252/455 |
| 3,130,007 A | 4/1964 | Breck | 23/113 |
| 4,310,440 A | 1/1982 | Wilson et al. | 252/435 |
| 5,558,767 A * | 9/1996 | Ressl | 208/105 |
| 5,739,072 A * | 4/1998 | Shi et al. | 502/72 |
| 5,798,313 A | 8/1998 | Carroll et al. | 502/38 |
| 6,455,748 B2 | 9/2002 | Janssen et al. | 585/638 |
| 6,482,999 B2 | 11/2002 | Fung et al. | 585/640 |
| 2004/0034264 A1 | 2/2004 | Janssen et al. | 585/639 |
| 2004/0034265 A1 | 2/2004 | Janssen et al. | 585/640 |
| 2006/0040821 A1 | 2/2006 | Pujado | 502/34 |

* cited by examiner

*Primary Examiner* — Edward Johnson
(74) *Attorney, Agent, or Firm* — Mark Goldberg

(57) ABSTRACT

The invention relates to a conversion process for making olefin(s) using a molecular sieve catalyst composition. More specifically, the invention is directed to a process for converting a feedstock comprising an oxygenate in the presence of a molecular sieve catalyst composition, wherein the air feed to the catalyst regenerator is free of or substantially free of metal salts. The air feed is preferably purified by passage through a rotary adsorbent contactor or adsorbent wheel.

15 Claims, No Drawings

TREATMENT OF AIR TO A CATALYST REGENERATOR TO MAINTAIN CATALYST ACTIVITY

CROSS-REFERENCE TO RELATED APPLICATION

This application is a Continuation-In-Part of copending U.S. application Ser. No. 11/287,032 filed Nov. 22, 2005, the contents of which are hereby incorporated by reference in its entirety.

FIELD OF THE INVENTION

The present invention relates to a conversion process for making olefin(s) using a molecular sieve catalyst composition in the presence of a hydrocarbon feedstock in which the air to the catalyst regeneration unit is dried to maintain catalyst activity. In a preferred embodiment of the present invention, the air to the catalyst regeneration unit is dried by use of at least one rotary adsorbent contactor or adsorbent wheel.

BACKGROUND OF THE INVENTION

The petrochemical industry has known for some time that oxygenates, especially alcohols, are convertible into light olefins. There are numerous technologies available for producing oxygenates including fermentation or reaction of synthesis gas derived from natural gas, petroleum liquids, carbonaceous materials including coal, recycled plastics, municipal waste or any other organic material.

The preferred methanol conversion process is generally referred to as a methanol-to-olefins (MTO) process, where methanol is converted primarily to ethylene and/or propylene in the presence of a molecular sieve which in turn can be used as the basic ingredients for polymers such as polyethylene and polypropylene. Molecular sieves have a crystalline pore structure with uniform sized pores of molecular dimensions that selectively adsorb molecules that can enter the pores, and exclude those molecules that are too large.

There are many different types of molecular sieves to convert a feedstock, especially a feedstock containing an oxygenate, into one or more olefins. For example, in U.S. Pat. No. 4,310,440 is disclosed a process of producing light olefin(s) from an alcohol using crystalline aluminophosphates, often represented by $ALPO_4$. The most useful molecular sieves for converting methanol to olefin(s) are silicoaluminophosphate molecular sieves.

These molecular sieves have been found to be sensitive to various contaminants resulting in the lowering of the yield of light olefins and even affecting the operability of a conversion process. Such contaminants are introduced to a particular conversion process in a variety of ways. Sometimes the molecular sieve itself produces contaminants affecting the conversion performance of the molecular sieve. In addition, in large scale processes, it is more likely that the effect of various contaminants entering into commercial conversion processes is higher. Contaminants can be introduced into the oxygenate feedstock or in the air that is introduced, especially into the catalyst regeneration unit. Unfortunately, it has been found that contaminants such as salts become concentrated over time to the extent that olefin yields are significantly impacted. In addition, the exposure of the catalyst to very high temperature steam in the regeneration unit has a significant contribution to the deactivation of the catalyst. We refer to this deactivation as "hydrothermal deactivation." Temperatures in the regeneration unit are typically about 625° C. or higher as compared to about 475° C. in a methanol-to-olefins reactor. Due to the adverse effects of these higher temperatures upon catalyst activity, in the present invention it has been found very important to keep the moisture level as low as reasonably possible within the regeneration unit.

Therefore, it would be highly desirable to control contamination so as not to adversely affect the molecular sieve catalyst. Controlling contamination is particularly desirable in oxygenate to olefin reactions, particularly in methanol to olefin reactions, where feedstocks and catalysts are relatively expensive. It has now been found highly desirable to dry the air to the regeneration unit in order to significantly reduce the rate of catalyst deactivation caused by exposure to steam in the regeneration unit.

In addition, it has been previously reported by Janssen et al. in US 2004/0034264 A1 and US 2004/0034265 A1 that feedstocks need to be free or substantially free of salts. However, it has now been found that serious damage to the catalyst can be caused by exposure of the catalyst to the sodium chloride that is present in the air in coastal areas such as where petrochemical plants are frequently located. The present invention provides a process to protect the catalyst from harm from this and other salts that may be unexpectedly present in the air entering the reactor and particularly regarding air entering the catalyst regeneration vessel.

SUMMARY OF THE INVENTION

The present invention relates to a process of regenerating a molecular sieve catalyst comprising: removing moisture and airborne salts from air prior to the air being sent into a catalyst regeneration unit, introducing a spent molecular sieve catalyst into the regeneration unit; and heating the molecular sieve catalyst for a sufficient period of time and at a sufficient temperature to regenerate said molecular sieve catalyst.

This invention provides for a process for converting a feedstock in the presence of a molecular sieve into one or more olefin(s), while controlling contamination of the catalyst. Contamination of the catalyst can be controlled by providing a regeneration air feed having an appropriately low content of moisture and salt.

The invention is directed to a process for converting a feedstock in the presence of a molecular sieve into one or more olefin(s). Preferably the feedstock comprises an oxygenate such as an alcohol and/or an ether, for example methanol and/or dimethyl ether. The preferred molecular sieve is synthesized from a combination of at least two, preferably at least three, of the group consisting of a silicon source, a phosphorous source and an aluminum source, optionally in the presence of a templating agent. In the most preferred embodiment, the molecular sieve is a silicoaluminophosphate or aluminophosphate, most preferably a silicoaluminophosphate.

These molecular sieve catalysts require periodic regeneration in order to maintain the catalyst activity. The catalyst regenerators need to have a stream of air entering the regenerator in order to provide the oxygen needed in burning off carbonaceous deposits on the catalyst. It has been found advantageous to remove water and salt from the air entering the regenerator. There are several effective methods for removing the moisture and salt. The air stream may be passed through a cooler in which water condenses and salt is removed along with the water and other contaminants. Another method for removing the water is to pass the air stream over an adsorbent bed in which again water is removed as well as salts and other contaminants. In a preferred embodiment, the water is removed by a rotary adsorbent contactor or an adsorbent wheel that is positioned so that the air stream passes through an adsorbent sector of the adsorbent wheel to be dried prior to passing through the regeneration unit. The adsorbent sector of the adsorbent wheel is regenerated as needed by a heated flow of dry gas, such as air, to remove water adsorbed in the adsorbent sector.

DETAILED DESCRIPTION OF THE INVENTION

The invention is directed toward a conversion process of a hydrocarbon feedstock, particularly methanol, in the presence of molecular sieve catalyst composition to one or more olefin(s). In this invention, gas fed to a catalyst regeneration unit is low in contaminants and particularly low in moisture and salts, so as not to significantly have an adverse effect on catalyst life or selectivity in conversion of the feed stream to produce the desired product.

According to this invention, some reduction in catalyst life is expected as a result of regeneration air containing contaminants, including contaminants that are present in the regeneration air due to exposure to seawater. These contaminants are more particularly water and Group IA and/or Group IIA metal contaminants such as sea borne salts. Generally, it is preferred that catalyst life be reduced by an amount of not greater than 20% relative to that of a regeneration air containing a low level of contaminants. Preferably, catalyst life is reduced by an amount of not greater, than 15%, more preferably not greater than 10% relative to that of a regeneration gas containing a low level of contaminants.

The catalysts used in methanol to olefins reactions is sensitive to high temperatures in the presence of moisture, which is also referred to as hydrothermal deactivation. Temperatures are higher in the regenerator (about 625° C. or more) and it is important at those temperatures to keep the moisture level as low as practically possible. The catalyst is also poisoned and deactivated by exchangeable metals in the feed, particularly sodium ions. Accordingly, steps need to be taken to eliminate any sodium that may be present in any feed streams to the reactor.

Typically, within the reactor, reaction conditions are about 475° C. at 138 kPa (20 psig) and about 60 mol-% steam in the reactor effluent, or about 1.4 bar abs. partial pressure of stream. This steam is generated as a reaction byproduct and cannot be reduced when the feed to the reactor is pure methanol. The only way to reduce the level of steam by control of the feed stream would be to feed dimethyl ether or dimethyl ether/methanol blends to the reactor. It has been calculated that, under standard reaction condition, the reactor operation contributes about 0.255% per day to the deactivation of the catalyst.

The methanol-to-olefins catalyst regenerator typically operates at an average temperature of about 625° C. and 138 kPa (20 psig). In the regenerator there are two sources of steam, the moisture that comes into the regenerator with the air and the steam generated by combustion of the hydrogen contained in the coke being burned off the catalyst. A typical coke formula is $CH_{1.6}$ to $CH_{1.8}$. If the air is moist, for example about 3.74 mol-% water and there is 30% excess oxygen, the flue gas will contain about 7.57 mol-% steam corresponding to a steam partial pressure of about 0.18 bar abs. Although this partial pressure of steam is much lower than the steam pressure in the reactor, the higher temperature in the regenerator has been calculated to result in a 60% contribution to the rate of deactivation of the catalyst which under these conditions is estimated to be about 0.67% per day (0.26% from the reactor and 0.41% from the regenerator).

In the present invention it has been found that the rate of deactivation can be reduced by drying the air going to the regenerator. When dry air is used, the flue gas will contain about 4.35 mol-% steam, corresponding to a partial pressure of about 0.10 bar abs., and resulting in an overall deactivation rate of about 0.50% per day (0.26% from the reactor and 0.24% from the regenerator. Therefore, the rate of catalyst deactivation is reduced by about 40%.

Another advantage of drying the air in the same operation is that it can then be feasible to also reduce the salinity of the inlet air. Many plants are likely to be located near a coast line where it is common to have saline aerosols present in the air. If the inlet air to the regenerator contains even 1 wt-ppb sodium, it would result in the buildup of about 1.0 to 1.5 ppm sodium on the catalyst within one year of operation. It is likely that the inlet air contains significantly more sodium than one part per billion with proportionately higher buildup of sodium on the catalyst. Sodium and other exchangeable metals are known to be irreversible catalyst poisons for the conversion of oxygenates to olefins because they neutralize active acid sites on the catalyst. An increase in sodium content leads to the progressive loss of catalyst activity. Therefore it is important to provide a means to dry the air and purify the air to the regenerator in order to decrease the rate of catalyst deactivation.

Catalysts suitable for catalyzing the oxygenate-to-olefin conversion reaction of the present invention include molecular sieve catalysts. Molecular sieve catalysts can be zeolitic (zeolites) or non-zeolitic (non-zeolites). Useful catalysts may also be formed from mixtures of zeolitic and non-zeolitic molecular sieve catalysts. Desirably, the catalyst is a non-zeolitic molecular sieve. Desired catalysts for use with the process of the present invention include "small" and "medium" pore molecular sieve catalysts. "Small pore" molecular sieve catalysts are defined as catalysts with pores having a diameter of less than about 5.0 angstroms. "Medium pore" molecular sieve catalysts are defined as catalysts with pores having a diameter in the range of from about 5.0 to about 10.0 angstroms. Properly adjusted acid strength, acidity distribution, and acid site density are also keys to a good oxygenate conversion catalyst.

Useful zeolitic molecular sieve catalysts include, but are not limited to, mordenite, chabazite, erionite, ZSM-5, ZSM-34, ZSM-48 and mixtures thereof. Methods of making these catalysts are known in the art and need not be discussed here.

Silicoaluminophosphates ("SAPOs") are one group of non-zeolitic molecular sieve catalysts that are useful in the present invention. Processes for making useful SAPOs are known in the art. In particular, small pore SAPOs are desired. SAPO type molecular sieves have a three-dimensional microporous crystalline framework of $PO_2+$, $AlO_2-$, $SiO_2$ and $MeO_2$ tetrahedral units, with or without metals in the framework. The superscript represents a net electric charge depending on the valence state of the substituent, Me. When "Me" has valence state of +2, +3, +4, +5, or +6 state, m is −2, −1, 0, +1, and +2, respectively. "Me" includes, but is not necessarily limited to, Zn, Mg, Mn, Co, Ni, Ga, Fe, Ti, Zr, Ge, Sn, Cr, and mixtures thereof. Because an aluminophosphate ($AlPO_4$) framework inherently is neutral in electrical charges, the incorporation of silicon or other metallic or nonmetallic elements into the framework by substitution generates more active catalytic sites, particularly acid sites, and increased acidity. Controlling the quantity and location of silicon atoms and other elements incorporated into an $AlPO_4$ framework is important in determining the catalytic properties of a particular SAPO-type molecular sieve. Suitable SAPOs for use in the invention include, but are not necessarily limited to, SAPO- 34, SAPO-17, SAPO-18, SAPO-44, SAPO-56 and mixtures thereof. In a more desired embodiment, the SAPO is SAPO-34.

Substituted SAPOs form a class of molecular sieves known as "MeAPSOs," which are also useful in the present invention. Processes for making MeAPSOs are known in the art. SAPOs with substituents, such as MeAPSOs, also may be suitable for use in the present invention. Suitable substituents, "Me," include, but are not necessarily limited to, nickel, cobalt, manganese, zinc, titanium, strontium, magnesium, barium, and calcium. Desired MeAPSOs are small pore MeAPSOs having pore size smaller than about 5 angstroms. Small pore MeAPSOs include, but are not necessarily limited to NiSAPO-34, CoSAPO-34, NiSAPO-17, CoSAPO-17, and mixtures thereof.

Aluminophosphates (ALPOs) with substituents, also known as "MeAPOs," are another group of molecular sieves that may be suitable for use in the present invention, with desired MeAPOs being small pore MeAPOs. Processes for making MeAPOs are known in the art. Suitable substituents include, but are not necessarily limited to nickel, cobalt, manganese, zinc, titanium, strontium, magnesium, barium, and calcium. The catalyst may be incorporated into a solid composition, preferably solid particles, in which the catalyst is present in an amount effective to promote the desired conversion reaction. The solid particles may include a catalytically effective amount of the catalyst and matrix material, preferably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. Such matrix, e.g., filler and binder, materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-alumina-zirconias, and mixtures of these.

Examples of the preferred molecular sieves for converting an oxygenate containing feedstock into olefin(s), include AEI, AEL, AFY, BEA, CHA, EDI, FAU, FER, GIS, LTA, LTL, MER, MFI, MOR, MTT, MWW, TAM and TON. In the preferred embodiment, the molecular sieve has an AEI topology or a CHA topology, or a combination thereof, most preferably a CHA topology.

The most preferred molecular sieves are silicoaluminophosphates that have eight rings and an average pore size less than about 5 angstroms, preferably in the range of from 3 to about 5 angstroms, more preferably from 3 to about 4.5 angstroms, and most preferably from 3.5 to about 4.2 angstroms.

The most preferred molecular sieves are SAPO molecular sieves, and metal substituted SAPO molecular sieves. The metal is selected from the group consisting of Co, Cr, Cu, Fe, Ga, Ge, Mg, Mn, Ni, Sn, Ti, Zn and Zr, and mixtures thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal-containing molecular sieves thereof.

Synthesis of molecular sieves is well known in the art. Generally, molecular sieves are synthesized by the hydrothermal crystallization of one or more of a source of aluminum, a source of phosphorous, and a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

The molecular sieve catalyst compositions described above are useful in a variety of processes including: cracking, for example, a naphtha feed to light olefin(s) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methylethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock containing an oxygenate, more particularly a feedstock containing an alcohol, is converted primarily into one or more olefin(s). The olefin(s) or olefin monomer(s) produced from the feedstock typically have 2 to 4 carbons atoms, with some higher carbon byproducts, and most preferably are ethylene and/or propylene. Examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. In the most preferred embodiment, the oxygenate feedstock, preferably an alcohol, most preferably methanol, is converted to the preferred olefin(s) ethylene and/or propylene.

The process of the present invention is generally referred to as gas-to-olefins (GTO) or alternatively, methanol-to-olefins (MTO). In an MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The amount of fresh liquid fed separately or jointly with a vapor feedstock, to a reactor system is in the range of from 0.1 to about 85 wt-%, preferably from about 1 to about 75 wt-%, more preferably from about 5 to about 65 wt-% based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. Cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred; however, gravity effects within the disengaging vessel will also separate the catalyst compositions from the gaseous effluent. Other methods for separating the catalyst compositions from the gaseous effluent include the use of plates, caps, elbows, and the like.

The disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system.

The conversion temperature employed in the conversion process, specifically within the reactor system, is in the range of from about 200° to about 1000° C., preferably from about 250° to about 800° C., most preferably from about 350° to about 550° C.

The conversion pressure employed within the reactor system varies over a wide range including autogenous pressure. The conversion pressure is based on the partial pressure of the feedstock exclusive of any diluent therein. Typically the conversion pressure employed in the process is in the range of from about 0.1 kPa to about 5 MPa, preferably from about 5 kPa to about 1 MPa, and most preferably from about 20 kPa to about 500 kPa.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than about 0.5 wt-% based on the total weight of the coked molecular sieve catalyst composition entering the regeneration system. The molecular sieve catalyst composition withdrawn from the regenerator forms a regenerated molecular sieve catalyst composition. Air being fed to a catalyst regenerator can be dried in order to reduce the level of hydrothermal damage on the catalyst due to the combination of moisture and high temperatures. For example, if the inlet air is humid with about 4.0 mol-% moisture content, the outlet gas from a regenerator will contain about 7.5 mol-% moisture. At 625° C., exposure of the catalyst to this hot and humid gas may result in a relative activity loss of about 0.4 to 0.6% per day. However, if the inlet air is dried, the offgas from the regenerator will only contain about 3.5 mol-% moisture. At 625° C., exposure of the catalyst to these conditions will result in a relative activity loss of about 0.1 to 0.3% per day.

We have found that there are several possible methods that can work to remove water from the inlet air. A drying wheel provides a low pressure drop and allows for the regeneration of the material used as adsorbent. The preferred adsorbents are zeolites. Zeolites are crystalline aluminosilicates with complex three dimensional infinite lattices. While some commercially used zeolites are natural minerals, most commercial zeolite adsorbents are produced synthetically. They are normally synthesized containing cations from group IA or IIA of the Periodic Table, in particular sodium, potassium, magnesium, and calcium. Chemically, zeolites are often represented by the empirical formula:

$$M_{2/n}O Al_2O_3 . y SiO_2 . w H_2O$$

whereby y is 2 or greater, n is the valence of the cation M, and w represents the water contained in the voids of the zeolite.

Zeolites are often classified by their crystal structure. The International Zeolite Association maintains a listing of known zeolite structures, and assigns a well known three letter designation for the structure. Commercially important zeolites include, zeolite A, described in U.S. Pat. No. 2,882,243, and given the designation LTA, and zeolite X described in U.S. Pat. No. 2,882,244, and zeolite Y, described in U.S. Pat. No. 3,130,007, both of which have the structure of the mineral faujasite, and have the designation, FAU, but with different ratios of silicon and aluminum in the framework lattice.

It is well known that the cations in the zeolite can be replaced by other cations by an ion exchange process. The affinity of a zeolite for a particular cation is known to vary with the structure, and the ratio of silicon and aluminum in the framework. The affinity of the zeolite for the cation determines the conditions needed to obtain the amount of exchange desired in the zeolite.

Many of these ion exchanged forms of zeolites are used commercially. The potassium form of LTA, known as 3A because the pore opening of the zeolite is reduced to approximately 3 angstroms, is often used as an adsorbent. It has gained favor over the sodium form of LTA, known as 4A, in drying the air space between dual pane windows because unlike 4A, its reduced pore size will not allow 3A to adsorb air at low temperature. The calcium exchanged form of LTA, 5A, is favored in iso-normal paraffin separations where a slightly larger pore size improves performance.

Many ion exchanged forms of FAU are also known. DDZ-70 is a rare earth exchanged form of FAU available from UOP LLC, Des Plaines, Ill. and is a preferred zeolite for use in the present invention.

In accordance with the present invention, a rotary adsorbent contactor (also known as an adsorbent wheel or desiccant wheel in some applications) is employed to dry, purify or separate components from the air stream entering the regenerator. A continuous system is provided for the purification of this air stream. The air passes through the rotary adsorbent contactor in a direction parallel to its axis of rotation. The surfaces exposed to the air flow comprise an adsorbent material. After being dried by passing through the rotary adsorbent contactor, the air is sent to the regeneration vessel. Applicants have also found that the air entering the regeneration vessel can be a significant source of undesired salt. For example, if the air salinity contains 0.5 ppm sodium, over time without catalyst withdrawals or additions, the level of sodium on the catalyst could reach about 4500 wt-ppm, which would result in a significant loss of active sites. Typically, the broad range of air salinity is from 10 to 500 wt-ppb sodium. More typically the air salinity is from 10 to 100 ppb sodium. Even more typically, the air salinity is from 20 to 50 ppb sodium or from 20 to 40 ppb sodium. If, for example, the air salinity can be reduced to 30 wt-ppb, the buildup of sodium on the catalyst under similar conditions would be only 20 to about 250 wt-ppm, which has no significant effect on the activity of the catalyst. More preferably, the air salinity is from 0 to 50 wt-ppb and even more preferably the air salinity is in a range from 0-20 wt-ppb or below measurable limits. For long-term catalyst stability, it is desirable to maintain the sodium level below 500 wt-ppm. The zeolite used in the rotary adsorbent contactor can be selected to ion exchange the sodium within an air stream found in coastal areas. Alternatively, a condenser can be used to first remove some water and the sodium as well as other impurities prior to contacting the rotary adsorbent contactor. Additional water can be first added to the air to wash out at least a portion of the sodium content followed by drying to remove added water as well as residual water. The rotary adsorbent contactor is regenerated by passing a suitable regeneration gas that is at a higher temperature through the rotary adsorbent contactor. This regeneration gas removes water and other volatile impurities from the rotary adsorbent contactor and usually will be designed to be exhausted to the outside atmosphere. Nonvolatile salts may be allowed to accumulate on the adsorbent.

Various other means are available to reduce the moisture and the salinity in the inlet air. For example, if the air is cooled down sufficiently, excess moisture will condense out and the air salinity will be entrained with the condensate. This is especially useful in treating the air going to cryogenic air separation plants, or similar, such that a side stream can be recovered for use as catalyst regenerent.

Adsorptive means can also be used, either in the form of low pressure drop fixed bed adsorbents that will remove both moisture and entrained aerosols of saline particles, and the adsorbent can later be regenerated. The rotary adsorbent contactors or "drying wheels" are considered the most efficient method of achieving the drying and purification of the air stream that is the purpose of the present invention.

The catalyst regeneration temperature in the regeneration unit is in the range of from about 200° to about 1500° C., preferably from about 300° to about 1000° C., more preferably from about 450° to about 750° C., and most preferably from about 550° to 700° C. The regeneration pressure is in the range of from about 103 to about 3448 kPa, preferably from about 138 to about 1724 kPa (20 to 250 psia), more preferably from about 172 to about 1034 kPa (25 to 150 psia), and most preferably from about 207 to about 414 kPa (30 to 60 psia). The preferred residence time of the molecular sieve catalyst composition in the regenerator is in the range of from about one minute to several hours, most preferably about one minute to 100 minutes, and the preferred volume of oxygen in the gas exiting the regenerator is in the range of from about 0.01 to about 5 mol-% based on the total volume of the gas. The gas exiting the regenerator will contain CO and $CO_2$ that result from the combustion of carbonaceous materials. Because of the presence of residual oxygen in the offgas, post-combustion of CO may take place in the gaseous phase.

The burning of coke is an exothermic reaction so that the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. In one embodiment, the cooler regenerated molecular sieve catalyst composition is returned to the regenerator in a continuous cycle, alternatively, a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent, which are all herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the reactor(s). In another embodiment, the regenerated molecular sieve catalyst composition withdrawn from the regeneration system is returned to the reactor(s) directly, preferably after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained.

The light olefins that are produced in the process of this invention are preferably polymerized into polymers such as polyethylene and polypropylene.

The invention claimed is:

1. A process of regenerating a spent SAPO or AlPO molecular sieve catalyst comprising:
   a) introducing a spent SAPO or AlPO molecular sieve catalyst into a regeneration vessel;
   b) introducing a flow of dried and purified gas into said regeneration vessel, wherein said gas comprises about 10 to 500 ppb alkali metal salt and wherein said gas contains at least 50% less water than prior to being subjected to a drying and purification step wherein said drying and purification step comprises passing said gas in an axial direction through a rotary adsorbent contactor to remove impurities including water and said alkali metal salt and then sending a purified gas flow to said regeneration vessel; and
   c) heating said spent SAPO or AlPO molecular sieve catalyst for a sufficient period of time and at a sufficient temperature to regenerate said molecular sieve catalyst.

2. The process of claim 1 wherein said drying and purification step comprises first sending water through said gas to remove said alkali metal salt and then drying said gas.

3. The process of claim 1 wherein said gas comprises about 10 to 100 ppb sodium from said alkali metal salt.

4. The process of claim 1 wherein said gas comprises about 20 to 50 ppb sodium from said alkali metal salt.

5. The process of claim 1 wherein said gas comprises about 20 to 40 ppb sodium from said alkali metal salt.

6. The process of claim 1 wherein prior to contacting said rotary adsorbent contactor, said gas flow is cooled and as water is condensed, said water and said alkali metal salt are removed from said gas flow.

7. The process of claim 1 wherein said gas is selected from the group consisting of oxygen, $O_3$, $SO_3$, $N_2O$, NO, $NO_2$, $N_2O_5$, air, air diluted with nitrogen, air diluted with carbon dioxide, oxygen and water, carbon monoxide, and hydrogen.

8. The process of claim 7 wherein said gas is air.

9. The process of claim 1 wherein said purification step comprises passing said gas through an adsorbent bed to remove impurities including water and salts followed by sending a resulting purified gas flow to said regeneration vessel.

10. The process of claim 1 wherein after regeneration said molecular sieve catalyst contacts a feedstock comprising an oxygenate.

11. The process of claim 10 wherein the feedstock comprises methanol.

12. The process of claim 1 wherein prior to purification said gas contains at least one lithium, sodium, or potassium salt.

13. The process of claim 12 wherein prior to purification said gas contains at least one halide salt of lithium, sodium, or potassium.

14. The process of claim 13 wherein prior to purification said gas contains at least one chloride salt of lithium, sodium, or potassium.

15. The process of claim 14 wherein prior to purification said gas contains sodium chloride.

* * * * *